United States Patent [19]

Lewis et al.

[11] 4,247,535

[45] Jan. 27, 1981

[54] MODIFIED CYCLODEXTRIN SULFATE SALTS AS COMPLEMENT INHIBITORS

[75] Inventors: Arthur J. Lewis, Nanuet; Seymour Bernstein, New York, both of N.Y.

[73] Assignee: American Cyanamid Company, Stamford, Conn.

[21] Appl. No.: 91,213

[22] Filed: Nov. 5, 1979

[51] Int. Cl.³ .................... A61K 31/70; C08B 37/02
[52] U.S. Cl. .................................. 424/180; 536/112; 536/118
[58] Field of Search ................ 536/112, 118; 424/180

[56] References Cited

U.S. PATENT DOCUMENTS

| 4,020,160 | 4/1977 | Bernstein et al. | 424/180 |
| 4,021,544 | 5/1977 | Nair et al. | 424/180 |
| 4,066,829 | 1/1978 | Nair et al. | 424/180 |

*Primary Examiner*—Johnnie R. Brown
*Assistant Examiner*—Blondel Hazel
*Attorney, Agent, or Firm*—Norton S. Johnson

[57] ABSTRACT

Modified cyclodextrin sulfate salts useful as complement inhibitors.

15 Claims, No Drawings

MODIFIED CYCLODEXTRIN SULFATE SALTS AS COMPLEMENT INHIBITORS

BACKGROUND OF THE INVENTION

The present invention resides in the concept of certain sulfated modified cyclodextrins and salts thereof, which are novel compounds, and their use as inhibitors of the complement system of warm-blooded animals.

U.S. Pat. No. 4,020,160 discloses cyclodextrin sulfate salts as complement inhibitors. U.S. Pat. No. 4,021,544 discloses sulfated oligosaccharides of the maltose series useful as complement inhibitors. U.S. Pat. No. 4,021,545 discloses inulin poly(H-sulfate) and salts thereof useful as complement inhibitors.

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935-938 (1968); Ann. Rev. Medicine, 19, 1-24 (1968); The John Hopkins Med. J., 128, 57-74 (1971); Harvey Lectures, 66, 75-104 (1972); The New England Journal of Medicine, 287, 452-454; 489-495; 545-549; 592-596; 642-646 (1972); Scientific American, 229, (No. 5), 54-66 (1973); Federation Proceedings, 32, 134-137 (1973); Medical World News, Oct. 11, 1974, pp. 53-58; 64-66; J. Allergy Clin. Immunol., 53, 298-302 (1974); Cold Spring Harbor Conf. Cell Proliferation 2/Proteases Biol. Control/229-241 (1975); Ann. Review of Biochemistry, 44, 697 (1974); Complement in Clinical Medicine, Disease-a-Month, (1975); Complement, Scope, December 1975; Annals of Internal Medicine, 84, 580-593 (1976); "Complement: Mechanisms and Functions", Prentice-Hall, Englewood Cliffs, N.J. (1976); Essays Med. Biochem., 2, 1-35 (1976); Hospital Practice, 12, 33-43 (1977); Perturbation of Complement in Disease, Chap. 15 in Biological Amplication Systems in Immunology (Ed. Day and Good), Plenum, New York and London (1977); Am. J. Clin. Pathology, 68, 647-659 (1977).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969); Journal of Immunology, 119, 1-8, 1195, 1358-1364, 1482 (1977).

A variety of substances have been disclosed as inhibiting the complement system, i.e., as complement inhibitors. For example, the compounds 3,3'-ureylenebis-[6-(2-amino-8-hydroxy-6-sulfo-1-naphthylazo)]benzenesulfonic acid, tetrasodium salt (chlorazol fast pink), heparin and a sulphated dextran have been reported to have an anticomplementary effect, British Journal of Experimental Pathology, 33, 327-339 (1952). German Pat. No. 2,254,893 or South African Pat. No. 727,923 discloses certain 1-(diphenylmethyl)-4-(3-phenylallyl)-piperazines useful as complement inhibitors. Other chemical compounds having complement inhibiting activity are disclosed in, for example, The Journal of Immunology, 93, 629-640 (1964); Journal of Medicinal Chemistry, 12, 415-419; 902-905; 1049-1052; 1053-1056 (1969); Canadian Journal of Biochemistry, 47, 547-552 (1969); The Journal of Immunology, 104, 279-288 (1970); The Journal of Immunology, 106, 241-245 (1971); The Journal of Immunology, 111, 1061-1066 (1973); Biochim. Biophys. Acta, 317, 539-548 (1973); Life Sciences, 13, 351-362 (1973); Journal of Immunology, 113, 584 (1974); Immunology, 26, 819-829 (1974);

Journal of Medicinal Chemistry, 17, 1160–1167 (1974); Biochim. Biophys. Res. Comm., 67, 225–263 (1975); Ann. N.Y. Acad. Sci., 256, 441–450 (1975); Journal of Medicinal Chemistry, 19, 634–639, 1079 (1976); Journal of Immunology, 118, 466 (1977); Arch. Int. Pharmacodyn., 226, 281–285 (1977); Biochem. Pharmacol. 26, 325–329 (1977); Journal Pharm. Sci., 66, 1367–1377 (1977); Chem. Pharm. Bull., 25, 1202–1208 (1977); Biochim. Biophys. Acts, 484, 417–422 (1977) and Journal Clin. Microbiology, 5, 278–284 (1977).

It has been reported that the known complement inhibitors epsilon-aminocaproic acid and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972), 287, 452–454 (1972); Ann. Interm. Med., 84, 580–593 (1976); J. Allergy and Clin. Immunology, 60, 38–40 (1977).

It has also been reported that the drug pentosanpolysulfoester has an anticomplementary activity on human serum, both in vitro and in vivo, as judged by the reduction in total hemolytic complement activity; Pathologie Biologie, 25, 33–36, 25 (2), 105–108, 25 (3), 179–184 (1977).

SUMMARY OF THE INVENTION

This invention is concerned with certain sulfated modified cyclodextrins and salts thereof, having complement inhibiting activity of the formula:

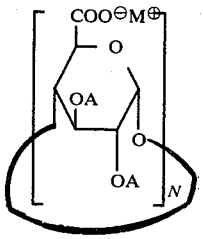

wherein M is a pharmaceutically acceptable salt cation; A is selected from the group consisting of hydrogen and $SO_3^{\ominus}M^{\oplus}$; and N is an integer from 6–8.

This invention, therefore, is concerned with α-cyclodextrins (N=6); β-cyclodextrins (N=7); and γ-cyclodextrins.

Operable pharmaceutically acceptable salts include, for example, those of alkali metals, alkaline earth metals, ammonium and amines such as triloweralkylamine ($C_1$–$C_6$), piperidine, pyrazine, alkanolamine ($C_1$–$C_6$) and cycloalkanolamine ($C_3$–$C_6$).

Specific compounds of the above formula which are of interest as complement inhibitors include, for example, the following:

5,5′,5″,5‴,5⁗,5⁗′,5⁗″-Heptacarboxy-6,6′,6″,6‴,6⁗,6⁗′,6⁗″-heptademethyl-β-cyclodextrin, heptasodium salt, tetradecakis(H-sulfate), tetradecasodium salt. [M=sodium; A—SO$_3$M; and N=7].

5,5′,5″,5‴,5⁗,5⁗′,5⁗″-Heptacarboxy-6,6′,6″,6‴,6⁗,6⁗′,6⁗″-heptademethyl-β-cyclodextrin, heptasodium salt. [M=sodium; A=hydrogen; and N=7].

This invention is also concerned with certain compounds which are intermediates for the preparation of the above complement inhibitors, some of which are themselves complement inhibitors and which may be represented by the formula:

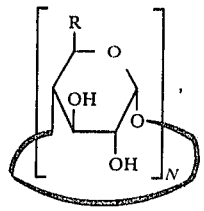

wherein R is selected from the group consisting of COOH and CHO; and N is an integer from 6–8.

Specific compounds of this latter formula which are of interest as intermediates for the preparation of complement inhibitors include, for example, the following:

5,5′,5″,5‴,5⁗,5⁗′,5⁗″-Heptacarboxy-6,6′,6″,6‴,6⁗,6⁗′,6⁗″-heptademethyl-β-cyclodextrin. [R=COOH; N=7].

6,6′,6″,6‴,6⁗,6⁗′,6⁗″-Heptademethyl-5,5′,5″,5‴,5⁗,5⁗′,5⁗″-heptaformyl-β-cyclodextrin. [R=CHO; N=7].

DESCRIPTION OF THE INVENTION

The complement inhibiting compounds of the present invention may be prepared by dissolving the modified cyclodextrin intermediates (prepared as described in Examples 1 and 3) and a sulfating agent in a solvent such as dimethylformamide, hexamethylphosphoramide or dimethylsulfoxide with heating at 40°–80° C. for a period of 6–24 hours. The molecular ratio of sulfating agent (e.g. trialkylammonium sulfur trioxide, or pyridinium sulfur trioxide), to the number of hydroxyl groups on the modified cyclodextrin determines the degree of sulfation. For complete sulfation an excess of sulfating reagent is used. The product can be isolated by adding a solvent such as acetone or methylene chloride and ether and the residue triturated with acetone or ether. The trialkylammonium or pyridinium sulfates of modified cyclodextrin can be converted to the alkali metal or ammonium salts by treatment with proper inorganic reagents such as sodium or potassium acetate or hydroxide in aqueous alcohol at room temperature or below as described in U.S. Pat. No. 2,923,704. The modified cyclodextrin sulfates of this invention may also be prepared from chlorosulfonic acid and sodium acetate as described in U.S. Pat. No. 2,923,704.

The compounds of the present invention may be administered internally, e.g., orally or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous of subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg. to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyl-dibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that those salts embrace, in general, derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form, as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3–C9 inhibitor)—This test determines the ability of the late components of human complement (C3–C9) to lyse EAC 142 in the presence of appropriate dilutions of the test compound. An active inhibitor protects EAC 142 from lysis by human C3–C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7-8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests code 026, 035, 036 and Cap 50. Table I shows that the compounds of the invention possess highly significant in vitro and in vivo complement inhibiting activity in warm-blooded animals. Results obtained are listed in Table I.

TABLE I

| Compound | Biological Activities | | | | In Vivo Activity (Guinea Pig) % Inhibition | | |
|---|---|---|---|---|---|---|---|
| | In Vitro Activity | | | | | | |
| | 026* | 035* | 036* | Cap 50* | 30 min. | 60 min. | 120 min. |
| 5,5′,5″,5‴,5⁗,5⁗′,5⁗″-Heptacarboxy-6,6′,6″,6‴,6⁗,6⁗′,6⁗″-heptademethyl-$\beta$-cyclodextrin | +5** | N | +1 | — | — | — | — |
| 5,5′,5″,5‴,5⁗,5⁗′,5⁗″-Heptacarboxy-6,6′,6″,6‴,6⁗,6⁗′,6⁗″-heptademethyl-$\beta$-cyclodextrin, heptasodium salt, tetradecakis (H-sulfate), tetradecasodium salt | +7 | +1 | +3 | 215 | −18 | +14 | −40 |
| 5,5′,5″,5‴,5⁗,5⁗′,5⁗″-Heptacarboxy-6,6′,6″,6‴,6⁗,6⁗′,6⁗″-heptademethyl-$\beta$-cyclodextrin, heptasodium salt | +2 | N | N | — | — | — | — |

*Code designation for tests employed as referred herein.
**Activity in wells, a serial dilution assay. Higher well number indicates higher activity. The serial dilutions are two-fold.
N = Negative

DETAILED DESCRIPTION OF THE INVENTION

The following examples describe in detail the preparation and formulation of representative compounds of the present invention.

EXAMPLE 1

5,5′,5″,5‴,5⁗,5⁗′,5⁗″-Heptacarboxy-6,6′,6″,6‴,6⁗,6⁗′,6⁗″-heptademethyl-$\beta$-cyclodextrin A 10.0 g portion of $\beta$-cyclodextrin and 75 ml. of carbon tetrachloride are placed in a 500 ml. round bottom flask equipped with three necks and a magnetic stir bar. A separate 500 ml. round bottom flask is charged with 90 ml. of nitrogen dioxide over 20 g. of 4A molecular sieves. The two flasks are then linked by glass tubing in a manner so that the glass tube extends below the liquid level in the flask containing the $\beta$-cyclodextrin-carbon tetrachloride mixture and above the liquid level in the flask containing the nitrogen dioxide. The $\beta$-cyclodextrin-carbon tetrachloride is then stirred, with cooling in an ice-water bath, while the flask containing the nitrogen dioxide is heated at 30°-40° C. In 2 hours the nitrogen dioxide is completely transferred and the reaction mixture is stirred at room temperature for 2 hours at which time a semi-solid mass accumulates on the side of the flask preventing further stirring. The carbon tetrachloride-nitrogen dioxide solution is removed and saved. The solid is scraped off the sides of the flask and the carbon tetrachloride-nitrogen dioxide solution is returned to the flask. The reaction is stirred for 67 hours giving a find green powder. The solid is recovered by filtration and washed with carbon tetrachloride until the filtrate is no longer colored brown. The white amorphous solid is dried in vacuo for 24 hours at room temperature followed by 24 hours at 80° C. giving the desired product as a pale yellow amorphous solid, mp 178°-179° C. (dec.).

EXAMPLE 2

5,5′,5″,5‴,5⁗,5⁗′,5⁗″-Heptacarboxy-6,6′,6″,6‴,6⁗,6⁗′,6⁗″-heptademethyl-$\beta$-cyclodextrin, heptasodium salt, tetradecakis (H-sulfate), tetradecasodium salt A 0.5 g. portion of 5,5′,5″,5‴,5⁗,5⁗′,5⁗″-heptacarboxy-6,6′,6″,6‴,6⁗,6⁗′,6⁗″-heptademethyl-$\beta$-cyclodextrin and 0.948 g. of trimethylamine-sulfur trioxide are added to 5 ml. of dimethylformamide. The mixture is heated in an oil bath at 70° C. for 17 hours. Absolute ethanol is added causing precipitation of a gummy residue which is triturated with absolute ethanol until solid. This solid is dissolved in 15 ml. of water and 2.5 ml. of 30% aqueous sodium acetate is added. The mixture is allowed to stand for 15 minutes, decolorizing charcoal is added and the mixture is filtered through diatomaceous earth, washed with water and the aqueous filtrate is poured into 400 ml. of absolute ethanol. The yellow precipitate that forms is recovered by filtration, washed with ethanol then ether and dried in vacuo at room temperature giving the desired product as a light brown amorphous solid.

EXAMPLE 3

6,6′,6″,6‴,6⁗,6⁗′,6⁗″-Heptademethyl-5,5′,5″,5‴,5⁗,5⁗′,5⁗″-heptaformyl-$\beta$-cyclodextrin A 10.0 g. portion of $\beta$-cyclo[6-azido-6-deoxy]dextrin, [H. Kurita, M. Kawazu and K. Takashima (Tanabe Seiyaku Co., Ltd.) Japan Kokai No., 74 85,015, Aug. 15, 1974 (Application No. 73 1537, Dec. 23, 1972); Chemical Abstracts, 82, 4533s (1975)], is dissolved in 300 ml. of a solution of 250 ml. of 2-methoxyethanol and 50 ml. of benzene. The mixture is placed under an argon atmosphere and then irradiated, without a filter, using a 450 watt Hanovia Type L mercury-arc lamp (Model 679A36 with a 4.5 inch arc). The lamp is cooled by use of a water cooled quartz immersion cell. Samples are taken at various times and analyzed by infra-red absorption spectrum for azide absorption. After 95 minutes, no azide absorption is detected and the irradiation is stopped. The mixture is filtered. The filtrate is evaporated in vacuo. The residue is dissolved in 50 ml. of water, cooled in ice-water and treated with 50 ml. of ice-cold one molar aqueous sulfuric acid for 30 minutes at 0°–5° C. The solution is neutralized with precipitated calcium carbonate, filtered, evaporated, redissolved in water and again filtered. The aqueous filtrate is poured into 500 ml of absolute ethanol. The resulting precipitate is recovered by filtration, washed with absolute ethanol and dried in vacuo, giving the desired product as a light brown amorphous solid.

EXAMPLE 4

5,5',5'',5''',5'''',5''''',5''''''-Heptacarboxy-6,6',6'',6''',6'''',6''''',6''''''-heptademethyl-β-cyclodextrin heptasodium salt A 2.0 g. portion of 6,6',6'',6''',6'''',6''''',6''''''-heptademethyl-5,5',5'',5''',5'''',5''''',5''''''-heptaformyl-β-cyclodextrin is dissolved in 300 ml. of 30% aqueous acetic acid containing 8 g. of sodium chloride. After 24 hours at room temperature, the mixture is dialyzed to remove inorganic salts. After dialysis, the solution is evaporated giving the desired product as a pale yellow glossy solid.

EXAMPLE 5

Preparation of Compressed Tablet

| Ingredient | mg/Tablet |
|---|---|
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 6

Preparation of Compressed Tablet - Sustained Action

| Ingredient | mg/Tablet |
|---|---|
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 7

Preparation of Hard Shell Capsule

| Ingredient | mg/Capsule |
|---|---|
| Active Compound | 0.5–500 |
| Lactose, Spray Dried | qs |
| Magnesium Stearate | 1–10 |

EXAMPLE 8

Preparation of Oral Liquid (Syrup)

| Ingredient | % W/V |
|---|---|
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 9

Preparation of Oral Liquid (Elixir)

| Ingredient | % W/V |
|---|---|
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 10

Preparation of Oral Suspension (Syrup)

| Ingredient | % W/V |
|---|---|
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 11

Preparation of Injectable Solution

| Ingredient | % W/V |
|---|---|
| Active Compound | 0.05–5 |
| Benzyl Alcohol N.F. | 0.9 |
| Water for Injection | 100.0 |

EXAMPLE 12

Preparation of Injectable Oil

| Ingredient | % W/V |
|---|---|
| Active Compound | 0.5–5 |
| Benzyl Alcohol | 1.5 |
| Sesame Oil qs ad | 100.0 |

EXAMPLE 13

Preparation of Intra-Articular Product

| Ingredient | Amount |
|---|---|
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 14

Preparation of Injectable Depo Suspension

| Ingredient | % W/V |
|---|---|
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |

-continued

Preparation of Injectable Depo Suspension

| Ingredient | % W/V |
|---|---|
| HCl to pH 6-8 | qs |
| Water for Injection qs ad | 100.0 |

EXAMPLE 15

Preparation of Dental Paste

| Ingredient | % W/V |
|---|---|
| Active Compound | 0.05-5 |
| Zinc Oxide | 15 |
| Polyethylene Glycol 4000 USP | 50 |
| Distilled Water qs | 100 |

EXAMPLE 16

Preparation of Dental Ointment

| Ingredient | % W/V |
|---|---|
| Active Compound | 0.05-5 |
| Petrolatum, White USP qs | 100 |

EXAMPLE 17

Preparation of Dental Cream

| Ingredient | % W/V |
|---|---|
| Active Compound | 0.05-5 |
| Mineral Oil | 50 |
| Beeswax | 15 |
| Sorbitan Monostearate | 2 |
| Polyoxyethylene 20 Sorbitan Monostearate | 3 |
| Methylparaben USP | 0.18 |
| Propyl Paraben USP | 0.02 |
| Distilled Water qs | 100 |

EXAMPLE 18

Preparation of Topical Cream

| Ingredient | % W/V |
|---|---|
| Active Compound | 0.05-5 |
| Sodium Laurylsulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 19

Preparation of Topical Ointment

| Ingredient | % W/V |
|---|---|
| Active Compound | 0.05-5 |
| Cholesterol | 3 |
| Stearyl Alcohol | 3 |
| White Wax | 8 |
| Petrolatum, White USP qs | 100 |

EXAMPLE 20

Preparation of Spray Lotion (non-Aerosol)

| Ingredient | % W/V |
|---|---|
| Active Compound | 0.05-5 |
| Isopropyl Myristate | 20 |
| Alcohol (Denatured) qs | 100 |

EXAMPLE 21

Preparation of Buccal Tablet

| Ingredient | g/Tablet |
|---|---|
| Active Ingredient | 0.00325 |
| 6 × Sugar | 0.29060 |
| Acacia | 0.01453 |
| Soluble Starch | 0.01453 |
| F.D. & C. Yellow No. 6 Dye | 0.00049 |
| Magnesium Stearate | 0.00160 |
| | 0.32500 |

The final tablet will weigh about 325 mg. and may be compressed into boccal tablets in flat faced or any other tooling shape convenient for buccal administration.

EXAMPLE 22

Preparation of Lozenge

| Ingredient | g/Lozenge |
|---|---|
| Active Ingredient | 0.0140 |
| Kompact ® Sugar (Sucrest Co.) | 0.7138 |
| 6x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

We claim:

1. A compound of the formula:

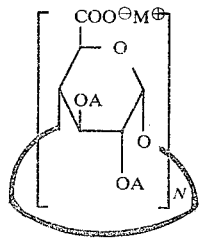

wherein M is a pharmaceutically acceptable salt cation; A is selected from the group consisting of hydrogen and $SO_3^{\ominus}M^{\oplus}$; and N is an integer from 6-8.

2. The compound according to claim 1, 5,5',5'',5''',5'''',5''''',5''''''-heptacarboxy-6,6',6'',6''',6'''',6''''',6''''''-heptademethyl-β-cyclodextrin, heptasodium salt, tetradecakis (H-sulfate), tetradecasodium salt.

3. The compound according to claim 1, 5,5',5'',5''',5'''',5''''',5''''''-heptacarboxy-6,6',6'',6''',6'''',6''''',6''''''-heptademethyl-β-cyclodextrin, heptasodium salt.

4. The compound 5,5',5'',5''',5'''',5''''',5''''''-heptacarboxy-6,6',6'',6''',6'''',6''''',6''''''-heptademethyl-β-cyclodextrin.

5. A method of inhibiting the complement system in a body fluid which comprises subjecting said body fluid to the action of an effective complement inhibiting amount of a compound of the formula:

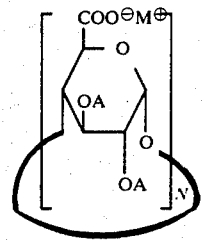

wherein M is a pharmaceutically acceptable salt cation; A is selected from the group consisting of hydrogen and $SO_3^{\ominus} M^{\oplus}$; and N is an integer from 6–8.

6. A method according to claim 5, wherein the body fluid is blood serum.

7. A method according to claim 5, wherein the compound is 5,5',5'',5''',5'''',5''''',5''''''-heptacarboxy-6,6',6'',6''',6'''',6''''',6''''''-heptademethyl-β-cyclodextrin, heptasodium salt, tetradecakis (H-sulfate), tetradecasodium salt.

8. A method according to claim 5, wherein the compound is 5,5',5'',5''',5'''',5''''',5''''''-heptacarboxy-6,6',6'',6''',6'''',6''''',6''''''-heptademethyl-β-cyclodextrin, heptasodium salt.

9. A method of inhibiting the complement system in a warm-blooded animal which comprises administering to said animal an effective complement inhibiting amount of a compound of the formula:

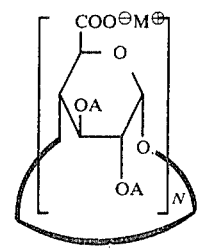

wherein M is a pharmaceutically acceptable salt cation; A is selected from the group consisting of hydrogen and $SO_3^{\ominus} M^{\oplus}$; and N is an integer from 6–8.

10. A method according to claim 9, wherein the compound is administered internally.

11. A method according to claim 9, wherein the compound is administered topically.

12. A method according to claim 9, wherein the compound is administered periodontally in the oral cavity.

13. A method according to claim 10, wherein the compound is administered intra-articularly.

14. A method according to claim 9, wherein the compound is 5,5',5'',5''',5'''',5''''',5''''''-heptacarboxy-6,6',6'',6''',6'''',6''''',6''''''-heptademethyl-β-cyclodextrin, heptasodium salt, tetradecakis (H-sulfate), tetradecasodium salt.

15. A method according to claim 9, wherein the compound is 5,5',5'',5''',5'''',5''''',5''''''-heptacarboxy-6,6',6'',6''',6'''',6''''',6''''''-heptademethyl-β-cyclodextrin, heptasodium salt.

* * * * *